US012765795B2

(12) United States Patent
Zeller

(10) Patent No.: US 12,765,795 B2
(45) Date of Patent: Oct. 20, 2026

(54) ASSESSMENT OF A MAGNETIC RESONANCE IMAGE-GENERATING PROCEDURE

(71) Applicant: Siemens Healthineers AG, Forchheim (DE)

(72) Inventor: Mario Zeller, Erlangen (DE)

(73) Assignee: Siemens Healthineers AG, Forchheim (DE)

( * ) Notice: Subject to any disclaimer, the term of this patent is extended or adjusted under 35 U.S.C. 154(b) by 541 days.

(21) Appl. No.: 18/222,624

(22) Filed: Jul. 17, 2023

(65) Prior Publication Data

US 2024/0016408 A1 Jan. 18, 2024

(30) Foreign Application Priority Data

Jul. 18, 2022 (DE) ..................... 10 2022 207 316.9

(51) Int. Cl.

| | |
|---|---|
| ***A61B 5/055*** | (2006.01) |
| ***A61B 5/00*** | (2006.01) |
| ***G01R 33/56*** | (2006.01) |
| ***G01R 33/561*** | (2006.01) |

(52) U.S. Cl.

CPC ............ *A61B 5/055* (2013.01); *A61B 5/0037* (2013.01); *A61B 5/7267* (2013.01); *G01R 33/5608* (2013.01); *G01R 33/5611* (2013.01); *A61B 5/7217* (2013.01); *A61B 5/742* (2013.01)

(58) Field of Classification Search

CPC ..... A61B 5/055; A61B 5/0037; A61B 5/7267; A61B 5/7217; A61B 5/742; G01R 33/5608; G01R 33/5611

See application file for complete search history.

(56) References Cited

U.S. PATENT DOCUMENTS

| | | | | |
|---|---|---|---|---|
| 2014/0232407 | A1* | 8/2014 | Nakamura | G01R 33/3621 324/322 |
| 2015/0241537 | A1* | 8/2015 | Dannels | G01R 33/56554 324/309 |
| 2016/0242712 | A1* | 8/2016 | Jin | A61B 6/5205 |
| 2017/0332981 | A1* | 11/2017 | Witschey | A61B 5/7289 |

(Continued)

OTHER PUBLICATIONS

Breuer, Felix A. et al. "General Formulation for Quantitative G-factor Calculation in GRAPPA Reconstructions", in: Magentic Resonance in Medicine, vol. 62, pp. 739-746, 2009 // DOI:10.1002/mrm.22066.

(Continued)

*Primary Examiner* — Ming Y Hon

(74) *Attorney, Agent, or Firm* — Banner & Witcoff, Ltd.

(57) ABSTRACT

A computer-implemented method for assessing an image-generating procedure of magnetic resonance imaging, wherein in the image-generating procedure, an image recording procedure using at least one accelerating technique is combined with a reconstruction procedure comprising a reconstruction function trained using machine learning, wherein the method includes: establishing a spatially resolved image quality metric for a magnetic resonance image generated with the image-generating procedure; evaluating the image quality metric using at least one measure criterion with which at least one notification and/or adaptation measure is associated; and carrying out the at least one notification and/or adaptation measure for each fulfilled measure criterion.

14 Claims, 3 Drawing Sheets

(56) References Cited

U.S. PATENT DOCUMENTS

| | | | | |
|---|---|---|---|---|
| 2018/0292491 | A1* | 10/2018 | Koch | G01R 33/583 |
| 2019/0066297 | A1* | 2/2019 | Middlebrooks | G06T 7/248 |
| 2022/0054010 | A1* | 2/2022 | Nishihara | A61B 5/7267 |
| 2023/0181117 | A1* | 6/2023 | Huijbers | A61B 5/11<br>600/301 |
| 2023/0184860 | A1* | 6/2023 | Chen | G01R 33/561<br>600/408 |
| 2023/0274562 | A1* | 8/2023 | Collazo | G06V 20/698<br>382/133 |
| 2023/0293037 | A1* | 9/2023 | Schmithorst | G01R 33/543<br>324/309 |
| 2024/0016408 | A1* | 1/2024 | Zeller | G01R 33/5608 |
| 2024/0257949 | A1* | 8/2024 | Wang | G06N 3/0985 |
| 2025/0321307 | A1* | 10/2025 | Wang | G01R 33/561 |
| 2025/0362361 | A1* | 11/2025 | Mallett | G01R 33/3802 |
| 2025/0375178 | A1* | 12/2025 | Aoyama | A61B 6/544 |

OTHER PUBLICATIONS

Hammernik, K., et al. "?—net: Systematic Evaluation of Iterative Deep Neural Networks For Fast Parallel MR Image Reconstruction", arXiv preprint arXiv:1912.09278 1 (2019).; 201.

Robson, Philip M. et al. "Comprehensive Quantification of Signal-to-Noise Ratio and g-Factor for Image-Based and k-Space-Based Parallel Imaging Reconstructions" Magnetic Resonance in Medicine, vol. 60, No. 4, pp. 895-907, 2008; 2008.

Han Y. et al. "k-Space Deep Learning for Accelerated MRI", arXiv:1805.03779v3 [cs.CV] Jul. 3, 2019.

Atsuro Suzuki et al. "ISMRM 2021 Deep-Learning-Based Noise Reduction Incorporating Inhomogeneous Spatial Distribution of Noise in Parallel MRI Imaging", Abstract #3264 (Feb. 22, 2023).

Wikipedia "Strukturelle Ähnlichkeit" / https://de.wikipedia.org/wiki/Strukturelle_%C3%84hnlichkeit—Stand: Jul. 2023.

* cited by examiner

ASSESSMENT OF A MAGNETIC RESONANCE IMAGE-GENERATING PROCEDURE

TECHNICAL FIELD

The disclosure relates to a computer-implemented method for assessing an image-generating procedure of magnetic resonance imaging, wherein in the image-generating procedure, an image recording procedure, in particular using at least one accelerating technique, is combined with a reconstruction procedure comprising a noise-reducing reconstruction technique using a reconstruction function trained using machine learning. In addition, the disclosure relates to a magnetic resonance apparatus, a computer program, and an electronically readable data carrier.

BACKGROUND

Magnetic resonance imaging is an often-used imaging modality, particularly in the medical field. Therein, oriented spins are excited in a main magnetic field (BO field), and the decay of the excitation is measured by means of a receiving coil arrangement. However, it is therein problematic that to generate magnetic resonance images, a very long timespan is needed, wherein in the present case, an image-generating procedure is to include both the actual image recording procedure in which raw data (magnetic resonance signals) is recorded in the k-space and the subsequent reconstruction procedure in which, in particular through transformation from the k-space into the image space, the actual magnetic resonance image is generated. Both with regard to the shortening of the scan time in the recording procedure and for optimizing the reconstruction time and reconstruction quality, in the prior art, many recording techniques and/or reconstruction techniques have previously been proposed.

The most frequent recording techniques (accelerating techniques) are the so-called compressed sensing (CS) and the so-called parallel acquisition technique (PAT). With compressed sensing, undersampling in the k-space is undertaken in a targeted manner to shorten the scan time. In parallel imaging, receiving coil arrangements are used, comprising a plurality of receiving coils, particularly surface coils and/or local coils, to be arranged close to the object that is to be recorded. The respective sensitivity profiles of these individual receiving coils are utilized to reduce the number of phase encoding steps during the recording procedure so that multiple reduction of the scan time is possible (acceleration factor). Herein, particularly complex reconstruction methods exist to the sensitivity information of the individual receiving coils to complement the undersampled data space. Examples of reconstruction techniques in this context comprise "sensitivity encoding for fast MRI" (SENSE), "simultaneous acquisition of spatial harmonics" (SMASH), and "generalized autocalibrating partially parallel acquisitions" (GRAPPA).

Regardless of which accelerating technique is utilized, the gain in speed often results in a greater level of noise, particularly a reduced signal-to-noise ratio (SNR). In parallel imaging, it can be said, for example, that the SNR with parallel imaging results as the SNR without acceleration divided by the root of the acceleration factor and divided by the so-called geometry factor (g-factor). The geometry factor defines a location-dependent noise amplification which depends, in particular, upon the number and position of the receiving coils, the coil loading, the imaging plane, the phase encoding direction, and the position of the respective image point (voxel).

The aim of the reconstruction, in particular when using accelerating techniques, is, despite any undersampling that may be present, to obtain magnetic resonance images that are as far as possible optimally suited for the imaging goal, for example, the diagnosis. For this reason, many reconstruction techniques have a noise-removing effect, either primarily or as a desired, accepted side-effect. With regard to the accelerating techniques, in particular parallel imaging, reconstruction techniques of artificial intelligence can lead to excellent imaging results but also provide for further acceleration of the image-generating procedure. Thus, reconstruction functions based upon deep machine learning can first carry out extremely fast reconstruction calculations and, secondly, permit the acceleration, particularly the acceleration factor, to be selected higher for the image recording procedure and, therefore, to achieve a further acceleration. For example, a reconstruction based upon neural networks from the k-space into the image space has been proposed by Kerstin Hammernik et al. in "I-net: Systematic Evaluation of Iterative Deep Neural Networks for Fast Parallel MR Image Reconstruction", arXiv:1912.09278v1, 18.12.2019. In an article by Yoseob Han et al., "k-Space Deep Learning for Accelerated MRI", arXiv:1805.03779v3, 03.07.2019, a k-space to k-space reconstruction was proposed.

Each reconstruction technique with a noise-removing effect carries the risk that structural information, in particular image content to be represented, becomes partially lost, which can occur particularly in heavily noise-laden regions. It has been found, in this regard, in particular with reconstruction functions trained using machine learning as described in the articles above, that with heavily noise-laden input data and, therefore, raw data in the k-space, in particular in regions in which with conventional reconstruction for parallel imaging a g-factor-based noise amplification would occur, a smoothing can take place.

Experiments have shown that these problems will likely arise if users wish to achieve extreme image generation time reductions by simultaneously setting extreme accelerations with the accelerating techniques and activating a reconstruction function trained by machining. Therein, regarding the accelerating technique, for example, extremely high acceleration factors can be set, for example, by adapting recording parameters in the scan protocol. Recording parameters of this type can relate, for example, to the reduction of the averagings and/or the setting of a high level of k-space undersampling. If a conventional reconstruction technique functioning without deep learning with a high phase oversampling level of 200% is used, a good overall impression in the resulting magnetic resonance image is brought about. If, however, a fourfold undersampling in the k-space is also included, a faded image impression can result. If, however, a trained reconstruction function based upon deep machine learning is used instead of the conventional reconstruction technique, despite the fourfold undersampling, the image sharpness of the magnetic resonance image is still exceeded with a fourfold reduction of the scan time. If, however, a fourfold undersampling of the k-space takes place with simultaneous reduction of the phase oversampling from 200% to 0%, therefore an acceleration by the factor 12, a conventional parallel imaging method would still only provide extremely noise-laden and thus unusable magnetic resonance images. If, in this regard, however, a reconstruction function trained by machine learning is engaged, this achieves an extremely clear, noise-reduced, sharp result in which however individual structural information items may be lacking. Disadvantageously, this can be overlooked such that a false assessment of magnetic resonance images can occur. This problem can also occur with other noise-removing reconstruction techniques.

SUMMARY

It is therefore an object of the disclosure to provide improved support to users carrying out image-generating processes in an accelerated manner, in particular, avoiding a faulty evaluation.

A method of the type mentioned in the introduction comprises the following steps:

- establishing an in particular spatially resolved, image quality metric for a magnetic resonance image generated with the image-generating procedure,
- evaluating the image quality metric by way of at least one measure criterion with which at least one notification and/or adaptation measure is associated,
- carrying out the notification and/or adaptation measure for each fulfilled measure criterion.

An approach is therefore proposed in which, in a first step, a metric for image quality is calculated, in a second step, the image quality metric is assessed, and in a third step, if necessary, an action takes place dependent upon the assessment achieved. For this purpose, at least one measure criterion is provided with which a measure is associated, such as a notification measure and/or an adaptation measure. The measure criterion evaluates the image quality metric, preferably determined as spatially resolved. Herein, it is provided, in particular, that at least one of the at least one measure criterion is checked for the presence of an excessively high risk of the failure to achieve an imaging goal, in particular, the at least partial loss of structural information that is to be imaged in the recording region by way of the accelerating technique and/or the noise reduction. In other words, the at least one measure criterion can infer, in particular from the image quality metric, whether by way of the noise-removing effect of the reconstruction technique, the risk arises of an information loss that is possibly unnoticed by the user since, for example, the existing database in the current embodiment, that is, the parameterization of the image-generating procedure is not sufficient or is falsely interpreted by the noise-reducing reconstruction technique. Generally formulated, therefore, an automatic assessment of the reconstruction result to be expected or achieved takes place, particularly in the context of a reconstruction utilizing deep machine learning (deep learning reconstruction). Since the greatest risk for an information loss occurs in the noise reduction, in particular by way of a noise-removing reconstruction function trained using machine learning, in which additional, in particular excessive, use of at least one accelerating technique, in particular, parallel imaging and/or compressed sensing occurs, the procedure described here is usable particularly advantageously in a combination of acceleration techniques in the image recording procedure and reconstruction functions in the reconstruction procedure that is trained based on deep machine learning.

In general, a trained function maps cognitive functions which humans associate with other human brains. Training based on training data (machine learning) allows the trained function to adapt to new circumstances and detect and extrapolate patterns.

In general, a trained function's parameters can be adapted through training, in particular, supervised learning, semi-supervised learning, unsupervised learning, reinforcement learning, and/or active learning can be used. In addition, representation learning (also known as "feature learning") can be used. The parameters of the trained function can be adapted in particular iteratively by way of a plurality of training steps.

A trained function can comprise, for example, a neural network, a support vector machine (SVM), a decision tree, and/or a Bayesian network, and/or the trained function can be based upon k-means clustering, Q-learning, genetic algorithms and/or assignment rules. In particular, a neural network can be a deep neural network, a convolutional neural network (CNN), or a deep CNN. Furthermore, the neural network can be an adversarial network, a deep adversarial network, and/or a generative adversarial network (GAN).

As measures in the context of the present disclosure, notification measures, adaptation measures, or a combination of both can be used. When fulfilling the measure criterion, notification measures draw a user's attention to the known image quality problem. This is particularly advantageous in that, for example, the absence of a structural information item, particularly where additional knowledge is unavailable, is typically not recognizable. By way of notification measures which can comprise, in particular, the output of a warning and/or a notification to the user, said user is made aware that in the existing parameterization of the image-generating procedure, problems with regard to the imaging goal can arise. He can now, for example, undertake reparameterizations himself, initiate renewed scans, and/or allocate a lower reliability to the evaluation in advance thereof. Adaptation measures which, in particular, can also be undertaken automatically, attempt with or without involving the user to reproduce the image quality necessary for the imaging goal, in particular by way of the adaptation of parameters of the image-generating procedure and/or, as will be set out in more detail below, an additional gain of raw data (magnetic resonance signals), in particular in an additional image recording procedure.

In this way, the procedure described here of the automatic assessment of the expected imaging quality, in particular with regard to the imaging goal, has the result that improved image quality is obtained in the magnetic resonance images, and assistance for the user is provided.

In principle, it is conceivable to establish the image quality metric before the start of the image recording procedure, in particular, based on magnetic resonance data from a prescan. In this regard, during the use of accelerating techniques, in particular compressed sensing and/or parallel imaging, as the image quality metric, in particular, the fundamental noise amplification is assessed by way of the accelerating technique, which, however, strongly correlates to the partially undesirable effects of noise-removing reconstruction techniques. Thus, as already described, it has been established that on use of reconstruction functions trained by way of machine learning in the context of parallel imaging, especially in particularly noise-amplified regions, an excessive smoothing of affected image regions in the magnetic resonance image can arise which, when establishing the image quality metric, can already be ascertained and evaluated even before the start of the image-generating procedure, in particular after a prescan.

In other words, the disclosure can suitably provide that the establishment and evaluation of the quality measure, and if at least one measure criterion is met, the execution of the associated notification and/or adaptation measure takes place before the execution of the image recording procedure, in particular directly following a prescan. In this way, before the actual recording of the raw data, it can already be ascertained whether problems could arise. Aside from a warning to a user, in particular, as an adaptation measure, an automatic adaptation of at least one image-generating parameter and/or as a combined notification and adaptation measure, a proposal for the adaptation of image-generating parameters, in particular of the scan protocol for the image recording procedure, can also take place.

Prescans are used, in particular, when accelerating techniques are utilized to be able to determine image-generating parameters, for example, reconstruction parameters. For example, the prescan can establish a sensitivity information item that describes the sensitivity of the receiving coil arrangement's receiving coils. During the prescan, in particular, a complete sampling of a lower region of the k-space to be sampled in the image recording procedure can occur. Typically, the lower region of the k-space to be sampled is situated about the k-space center.

It should be noted at this point that the, in particular spatially resolved, image quality metric must not necessarily relate to the entire recording region in the image space, but can naturally be restricted to regions of interest (ROI) with regard to the imaging goal. Thus, it can be provided that the image quality metric is established restricted to a region of interest of the recording region established, in particular, from a prescan and/or specified by the user, and/or the evaluation is restricted to the region of interest by way of at least one of the at least one measure criterion. For example, a check of whether too high a risk of a structural information loss exists can be restricted to the at least one region of interest. To establish the at least one region of interest, in particular by means using resonance data from the prescan, a mask of this region of interest can be established as a relevant examination region and then used in the establishment of the image quality metric and/or in the use of at least one of at least one measure criterion.

It should be noted at this point that the application of the method described here is not restricted to the application of artificial intelligence, which additionally acts in a noise-reducing manner, in particular in combination with accelerating techniques, but can also relate to cases in which a (targeted) noise reduction technique is used as a noise-reducing reconstruction technique and/or an accelerating technique is not used. Then, however, with the reconstructable, non-noise-reduced comparison image, a comparison basis exists from which, for example, conclusions can already be drawn regarding the loss of a structural information item or at least the risk thereof in comparison with the magnetic resonance image. In other words, it can be provided that, in particular with a noise reduction technique as the reconstruction technique and/or with non-use of an accelerating technique, the image quality metric is established from a comparison of a comparison image reconstructed without noise reduction from the same raw data with the magnetic resonance image, in particular as a similarity map. Nevertheless, since problems in a practice-relevant embodiment occur mainly in the combination of accelerating techniques and deep learning reconstructions, the following examples are directed mainly to this application area but without justifying a fundamental restriction on the usability of the procedure.

In general, exemplary embodiments of the present disclosure can provide that the image quality metric is established from magnetic resonance data of a prescan, in particular comprising a complete sampling of a lower region of the k-space to be sampled in the image recording procedure and/or for establishing reconstruction parameters to be used in the reconstruction procedure, for example from a sensitivity information item and/or from the magnetic resonance image. As already stated in relation to the general discussion of prescans above, the prescan can serve, particularly in accelerating techniques such as parallel imaging and/or compressed sensing, to establish sensitivity information from the at least one receiving coil of the receiving coil arrangement. In this context, different embodiments are now conceivable. Whenever merely the magnetic resonance data of the prescan is needed to establish the image quality metric, the assessment described above of the image quality to be expected before recording the raw data is, in particular, possible with the stated advantages.

Thus, a particularly advantageous embodiment of the present disclosure in which, in particular, the establishment and evaluation of the image quality metric can take place immediately after the prescan, that is, before the image recording procedure, can provide that as the image quality metric, a geometry factor map and/or a noise map and/or an SNR map of the signal-to-noise ratio is established, in particular only from the magnetic resonance data of the prescan. Calculation algorithms with which a geometry factor (g-factor) map can be established purely from magnetic resonance data of a prescan have previously been proposed in the prior art and can also be used in the context of the present disclosure. Purely by way of example for GRAPPA parallel imaging, but with corresponding mention of SENSE and SMASH, reference is made to the article by Felix A. Breuer et al., "General Formulation for Quantitative G-factor Calculation in GRAPPA Reconstruction," Magnetic Resonance in Medicine 62 (2009), pages 739 to 746. Such a geometry factor map indicates the in particular image point-based noise amplification by way of parallel imaging as an accelerating technique. In a similar, fundamentally known manner, magnetic resonance data from the prescan can also be evaluated to establish noise maps and/or SNR maps, that is, maps of the signal-to-noise ratio. In particular, in the context of noise-reducing reconstruction techniques, which include reconstruction functions trained by way of machine learning, in particular in accordance with the articles by K. Hammernik et al. and Y. Han et al. mentioned in the introduction, the noise amplification by way of the parallel imaging and the noise reduction of the trained reconstruction function related to the risk of loss of structural information are strongly correlated, so that the necessary conclusions can be drawn, so that for example measure criteria, which will be considered in more detail, can check whether too many excessively high g-factors occur and/or for large coherent regions, excessively high g-factors exist. Put another way, in such exemplary embodiments of the present disclosure, the fundamental noise amplification by way of parallel imaging can be assessed. However, as described above, it strongly correlates to the performance of the trained reconstruction functions.

In particular, if the reconstruction procedure is also included in establishing the image quality metric, the magnetic resonance image (following the generation thereof) can be drawn upon as at least part of the basis for establishing the image quality metric.

In this regard, a suitable development provides that a confidence map of the magnetic resonance image is established as the image quality metric, particularly using a trained confidence establishment function. Directed as it is to risks of non-fulfillment of the imaging goal, in particular the potential loss of structural information, the confidence map established also represents a useful means for assessing the image quality with regard to the imaging goal. Since the reliability information possibly also supplied by trained reconstruction functions mostly relates to the internal data processing, establishing the confidence map can be directed specifically to the question of relevance here, particularly an excessive noise-reduction which possibly destroys structural information.

In a specific embodiment, it can be provided that a confidence establishment function provided in addition to the trained reconstruction function is trained by machine learning, wherein the confidence establishment function establishes an associated confidence map from the magnetic resonance image. For example, training the confidence establishment function can take place such that it detects excessively smooth regions and/or other image features that imply excessively strong noise reduction and assesses them with correspondingly low confidence. Apart from the magnetic resonance image, the confidence establishment function can also use further input data, for example, other image quality metrics, such as geometry factor maps. The trained confidence establishment function can preferably be a deep neural network, particularly a CNN.

In one embodiment, it can be provided that the magnetic resonance image is cut to size to the lower region. By comparison with the magnetic resonance data of the prescan, a first similarity map is established as the image quality metric. Following the reconstruction procedure, in particular making use of the trained reconstruction function, a cutting to the size of the reconstructed k-space to the size of the lower region of the k-space that is to be sampled and was sampled in the prescan can therefore take place. Subsequently, the image spaces of the cut-to-size magnetic resonance image and of the prescan are investigated for deviations, wherein as a similarity measure for the first similarity map, for example, the structural similarity can be used. Since the prescan typically contains a complete sampling, by way of the comparison, it can easily be ascertained where excessive deviations are present, which can indicate, in particular, the loss of structural information.

In a related approach, it can also be provided that in addition to the establishment of the magnetic resonance image using the reconstruction procedure, an establishment of a comparison image takes place in a reconstruction procedure without using the noise-reducing reconstruction technique and by way of a comparison of the comparison image with the magnetic resonance data of the prescan and/or with the magnetic resonance image, at least one second similarity map is established. This approach is oriented to the idea that, in particular by way of excessive use of accelerating techniques, the raw data is already extremely incomplete and/or noise-laden, which, in particular in the use of trained reconstruction functions, is one of the main causes of the failure to achieve the imaging goal, in particular the lack of structural information. The noise-removing reconstruction technique, particularly the trained reconstruction function, provides a reconstruction result with the magnetic resonance image, which no longer has this problem. This means that in cases where such an information loss problem arises, there is a huge difference in the image impression both between the (indeed, in particular, not undersampled) prescan and the comparison image, as well as between the magnetic resonance image and the comparison image, so that the second similarity map, which can also use the structural similarity as the similarity measure, by way of a comparison of the "conventional reconstruction," that is of the comparison image, with the magnetic resonance data of the prescan and/or with the deep learning reconstruction, that is the magnetic resonance image, can be established.

If at least one such map, thus, in particular, a geometry factor map and/or a noise map and/or an SNR map and/or a confidence map and/or a first similarity map and/or a second similarity map, is established as a spatially-resolved image quality metric, the at least one measure criterion can provide in particular the use of threshold values which can be established for example empirically and/or analytically and/or by way of evaluating test measurements. A decision as to whether the measure criterion is fulfilled can then, therefore, take place accordingly, for example, based on at least one g-factor threshold value, at least one noise threshold value, at least one SNR threshold value, at least one confidence threshold value and/or at least one similarity threshold value.

In a suitable embodiment, it can be provided that at least one of the at least one measure criterion checks for at least one of the at least one map of the image quality metric whether

- at least one first threshold value is exceeded or undershot for at least one image point of the map and/or
- at least one second threshold value is exceeded or undershot for at least one specified proportion of the image points and/or
- whether the size of at least one cluster of image points, in which a third threshold value is exceeded or undershot, exceeds a fourth threshold value.

Therefore, a great variety of variants for the specific design of measure criteria is conceivable. A variant that is easy to implement is therein represented by a threshold value comparison with the first threshold value since it can then be sufficient if a first threshold value at a site indicates a risk of not reaching the imaging goal, in particular, the loss of structural information, in particular therefore at an image point of the at least one map for which it is to be used, is exceeded or undershot. Preferably a type of histogram analysis can be undertaken against this in that it is checked whether at least one specified, in particular, percentage, the proportion of the image quality values in the corresponding map exceeds a second threshold value. For this purpose, the image quality values can be arranged in a histogram, for example, in ascending order. It can then easily be checked whether a proportion of the image quality values, for example, geometry factors, specified in advance lie above a selected second threshold value, indicating a high risk of failure to achieve an imaging goal. In a particularly advantageous embodiment, at least one map can be investigated for clusters in which the image quality values exceed and/or undershoot a third threshold value and whether its size exceeds a fourth threshold value. Naturally, with regard to the first, second, or third threshold value, dependent upon the image quality value being observed, an undershooting can also be observed, for example, with confidence values and/or similarity measures.

Therein, the checking for clusters exceeding the third threshold value is particularly preferred since then it can be ascertained whether the exceeding is present in large coherent regions in the image space, since then a risk that features, that is, structural information, are completely suppressed and/or are not recognizable is also mapped.

As mentioned above, the at least one notification measure can suitably comprise an output of a warning and/or a notification to a user. This is particularly useful if the establishment of the image quality metric and its assessment can take place even before the actual scan, in particular, based on magnetic resonance data from the prescan, since then a main scan leading to unsuitable results can be prevented in that the user is notified thereof in advance. But also, retrospectively, if the magnetic resonance image has already been generated, a warning and/or a notification to a user can still be useful since he can better judge and appraise his image result. The output of a warning and/or a notification is furthermore also suitable in the context of an adaptation since, in the case of an automatic adaptation, the user can be informed and/or in the case of an adaptation still to be confirmed by a user, he can do so on a suitably informed basis.

In a particularly suitable development of the present disclosure, it can be provided that at least one notification and/or adaptation measure comprises the establishment of at least one proposal for at least one image-generating parameter that is to be amended of the image-generating procedure in particular at least one recording parameter of the recording procedure and/or at least one reconstruction parameter of the reconstruction procedure, wherein the proposal is used automatically and/or after confirmation by a user after an output to the user for adapting the image-generating parameters and an image generation takes place using the adapted image-generating parameters. Recording parameters can comprise in particular acceleration parameters, for example, undersampling parameters. Thus, for example, in the use of compressed sensing, the degree of undersampling can be adapted, in particular, reduced. In contrast, in parallel imaging, for example, the phase oversampling can be increased to improve the image quality, in particular in the context of the noise-reducing reconstruction technique.

Reconstruction parameters can comprise, for example, at least one regularizing factor and/or a noise-removal level and/or at least one mask, for example, a mask for sensitivity maps and/or at least one k-space mask. Herein, an adaptation can thus be directed in particular to reducing the noise reduction and thus lessening the risk of a failure of the imaging goal, particularly the loss of structural information. Other adaptations of reconstruction parameters can also force the receiving and/or the emphasis of the structural information. Dependent upon the noise-reducing reconstruction technique, other reconstruction parameters can be adapted, for example, with trained reconstruction functions of the corresponding noise-reducing parameters, said reconstruction functions being parameterizable with regard to the noise reduction. Particularly with regard to the adaptation of recording parameters for the image recording procedure, it is also particularly suitable if the relevant adaptation and/or adaptation occurring after user confirmation takes place even before the start of the image recording procedure, for example, based on an image quality metric established from magnetic resonance data of a prescan, as set out.

The establishment of the proposal can therein take place specifically such that at least the previously fulfilled measure criterion is no longer fulfilled when using the proposal; in particular, no further measure criterion is fulfilled. The proposal can thus be directed, even if possibly the image generating time increases, to reduce the risk of non-mapped structural information that is relevant at least to an acceptable level. For this purpose, it can be the aim of the proposal in particular that, following its implementation, no further measure criteria are fulfilled, so that in particular, even on establishment of the proposal, image quality metrics for the image generating result then a rising can be calculated in advance and/or at least estimated.

Suitably, in this context, it can be provided that for the at least one proposal, in particular the plurality of proposals, using the magnetic resonance data of the prescan, proposal image quality metrics are established and are visualized to a user for selection of at least one of the at least one proposal regarding, in particular, recording parameters. In a specific embodiment, for example, on establishment of a geometry factor map and/or a noise map and/or an SNR map from magnetic resonance data of a prescan for different other recording parameters, in particular acceleration parameters that are to be used as proposals, an additional establishment of proposed image quality metrics, therefore, for example, corresponding maps, can take place. If, for example, geometry factor maps are observed, then in advance, in particular before the start of the image recording procedure, a g-factor calculation for at least one possible adapted recording parameter, in particular an adapted scan protocol of the image recording procedure, can take place, wherein b-factor maps of different proposals can be presented to a user, for example as mean value, percentiles or using color-coding, to be able to offer a decision basis for the user-controlled selection and/or acceptance of a proposal. For example, different steps of the reduction of an undersampling in an accelerating technique can be investigated and presented accordingly so that, for example, a geometry factor distribution appearing suitable to the user can be selected. In particular, therefore, a color-coded representation of at least one map used as the image quality metric and thus also as a proposal image quality metric is conceivable.

As previously mentioned, however, it is in principle, also conceivable to select a suitable value entirely automatically, for example, for the undersampling, the value of a corresponding acceleration parameter as a recording parameter which permits the greatest possible undersampling without fulfilling one of the measure criteria. Therein, even with such an automatic adaptation, it is naturally suitably conceivable to output a corresponding notification to the user.

In a particularly advantageous embodiment of the disclosure, it can be provided that an improvement image is generated in a renewed reconstruction procedure for exclusively at least one proposal regarding reconstruction parameters. An improvement image quality metric is established, wherein for an improvement image quality metric indicating an improvement relative to the original image quality metric of the magnetic resonance image, the original magnetic resonance image is discarded. The improvement image is used as the magnetic resonance image. In this regard, an improvement of this type can also take place iteratively, particularly in an optimization method. If, for example, particular reconstruction parameters, for example, at least a regularization factor and/or a noise-reduction level and/or a mask are amended, a renewed reconstruction can be carried out with these amended reconstruction parameters. Subsequently, a re-assessment of the result now obtained takes place. If there is an improvement, the previous result can be discarded, and the newly generated result can be used as a magnetic resonance image. Optionally, an iterative change of parameters can take place until there is an optimal result. The changing of reconstruction parameters for proposals to be implemented automatically in the context of an adaptation measure has the advantage that no renewed or additional recording of raw data must take place if, in this way, an image-generating result having sufficient quality can be obtained. With the final magnetic resonance image, it can also be suitable to notify a user that changes have been made.

It is also conceivable that at least one adaptation measure relates to recording additional raw data, particularly reducing the undersampling in an additional recording procedure. This means, in particular, on assessment only after conclusion of the image-generating procedure, that it is conceivable to record complementary k-space data, that is, raw data, to reduce the effective undersampling. With this additional raw data, a renewed reconstruction procedure can be carried out to assess again the improvement then arising in the image quality metric to carry out, for example, other adaptation measures if necessary or, if useful, also to undertake a supplementation until, in particular, no further measure criterion is fulfilled. Thus, the whole recording of raw data does not have to be repeated, but rather it can be supplemented.

It should also be noted at this point that the image quality metric can suitably, in principle, be output to a user to inform him and, in particular, better to motivate adaptation measures that have been undertaken. For example, at least one established map, particularly a geometry factor map and/or a noise map and/or an SNR map and/or a confidence map, and/or a similarity map, can be visualized, for example, by way of color coding or suchlike. Given a spatially resolved image quality metric, it is also conceivable to establish and output representative values, for example, mean values.

Apart from the method, the present disclosure also relates to a magnetic resonance apparatus having a control apparatus designed for carrying out a method according to the disclosure. All the embodiments relating to the method according to the disclosure can be transferred similarly to the magnetic resonance apparatus according to the disclosure so that the aforementioned advantages can therefore also be achieved therewith.

In particular, the control apparatus can comprise at least one processor and at least one storage means. By way of hardware and/or software, functional units can be realized which can implement steps of the method according to the disclosure. For example, as is known in principle, the control apparatus can have a recording unit that controls the recording operation of the magnetic resonance apparatus, in particular therefore also the recording of the raw data during the image recording procedure and/or the recording of the magnetic resonance data of the prescan. The recording apparatus can also comprise an establishing unit for establishing the image quality metric, an evaluating unit for evaluating the fulfillment of the at least one measure criterion and a measuring unit for carrying out the at least one notification and/or adaptation measure of at least one fulfilled measure criterion. According to the disclosure, corresponding functional units can naturally be provided to realize further advantageous embodiments of the method.

A computer program according to the disclosure is able to be loaded directly into the memory store of a control apparatus of a magnetic resonance apparatus and has program means to carry out the steps of a method according to the disclosure when the computer program is executed in the control apparatus of the magnetic resonance apparatus. The computer program can be stored on an electronically readable data carrier which therefore comprises control information stored thereon, which comprises at least one computer program according to the disclosure and is designed such that, on use of the data carrier in a control apparatus of a magnetic resonance apparatus, during execution, it causes said control information to carry out a method according to the disclosure.

BRIEF DESCRIPTION OF THE DRAWINGS

Further advantages and details of the present disclosure are disclosed in the following description of exemplary embodiments and by reference to the drawings. In the drawings.

DETAILED DESCRIPTION

Exemplary embodiments of the present disclosure will now be described for cases in which a greatly accelerated magnetic resonance imaging process is desired. For this purpose, in an image-generating procedure comprising an image recording procedure and a reconstruction procedure, firstly at least one accelerating technique is utilized, in the present case at least parallel imaging, but alternatively or additionally compressed sensing. This at least one accelerating technique is combined with the use of a reconstruction function trained by way of deep machine learning, that is, a deep learning reconstruction, wherein for example the approaches described in the articles by K. Hammernik et al. and Y. Han et al. can be used to achieve outstanding image quality by rapid means. The deep neural networks used there as trained reconstruction functions additionally have a noise-removing, that is a noise-reducing, effect. This can also be capable of parameterization. If, by way of a suitable selection of recording parameters for the image recording procedure, an excessively strong acceleration is achieved, for example, too high an acceleration factor, then as is known, the signal-to-noise ratio, which is differently defined locally by the geometry factor (g-factor), falls. For example, in image space regions with a high geometry factor, the suppression of features in the recording region, in particular a region of interest, that are actually relevant for the imaging goal and therefore the loss of (relevant) structural information can occur. For example, a complete smoothing can occur in regions with a high geometry factor.

It is with this problematic effect of noise-reducing reconstruction techniques, trained reconstruction functions which herein act in a noise-reducing manner, that the solution approach described here concerns itself and offers, by way of assessing suitable image quality metrics and corresponding measures dependent upon this assessment, support to a user leading to him being better informed and/or, even automatically to an improved image quality with regard to the imaging goal.

Figure 1:
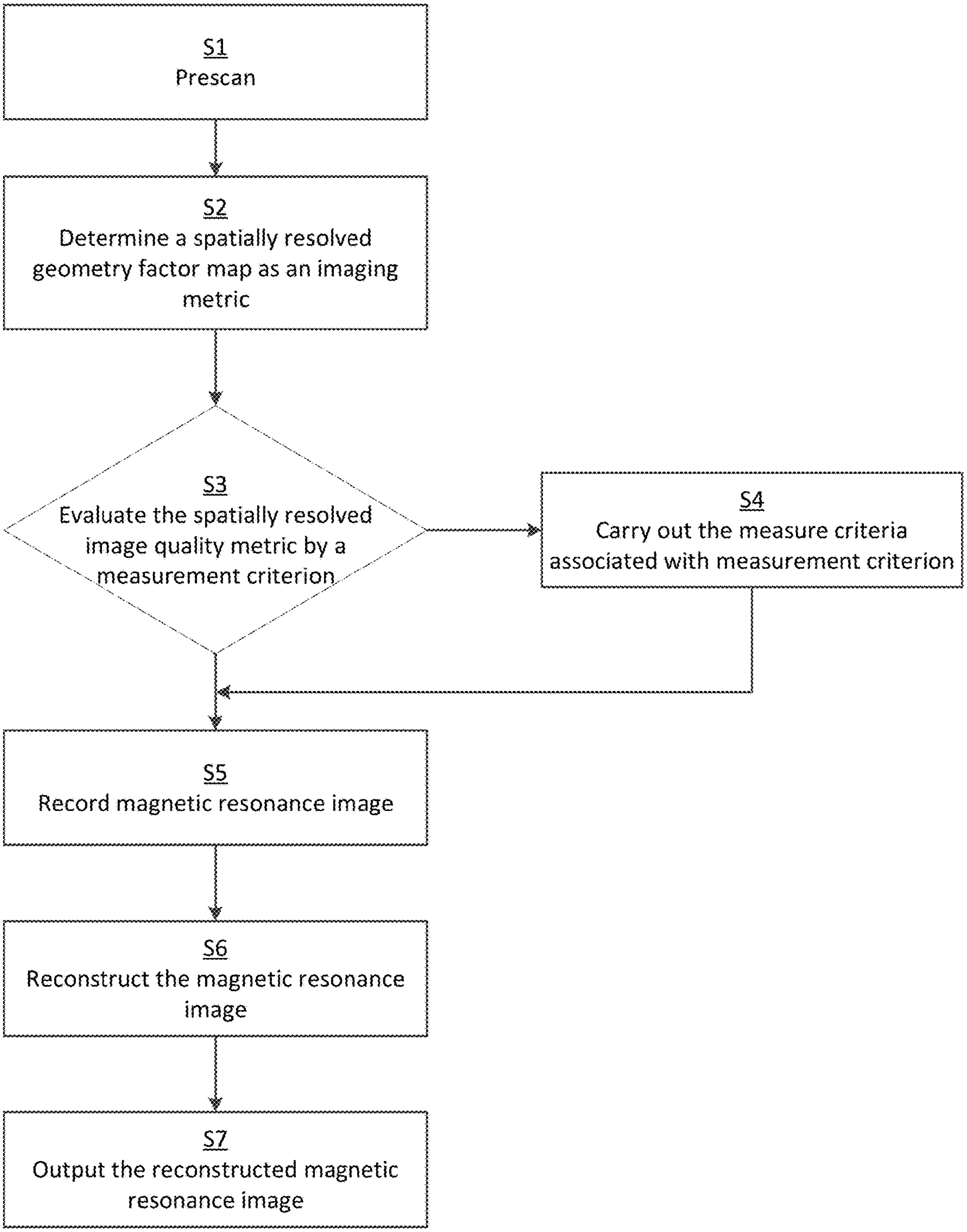
FIG. 1 shows a flow diagram of a first exemplary embodiment of the method according to the disclosure.
Figure 2:
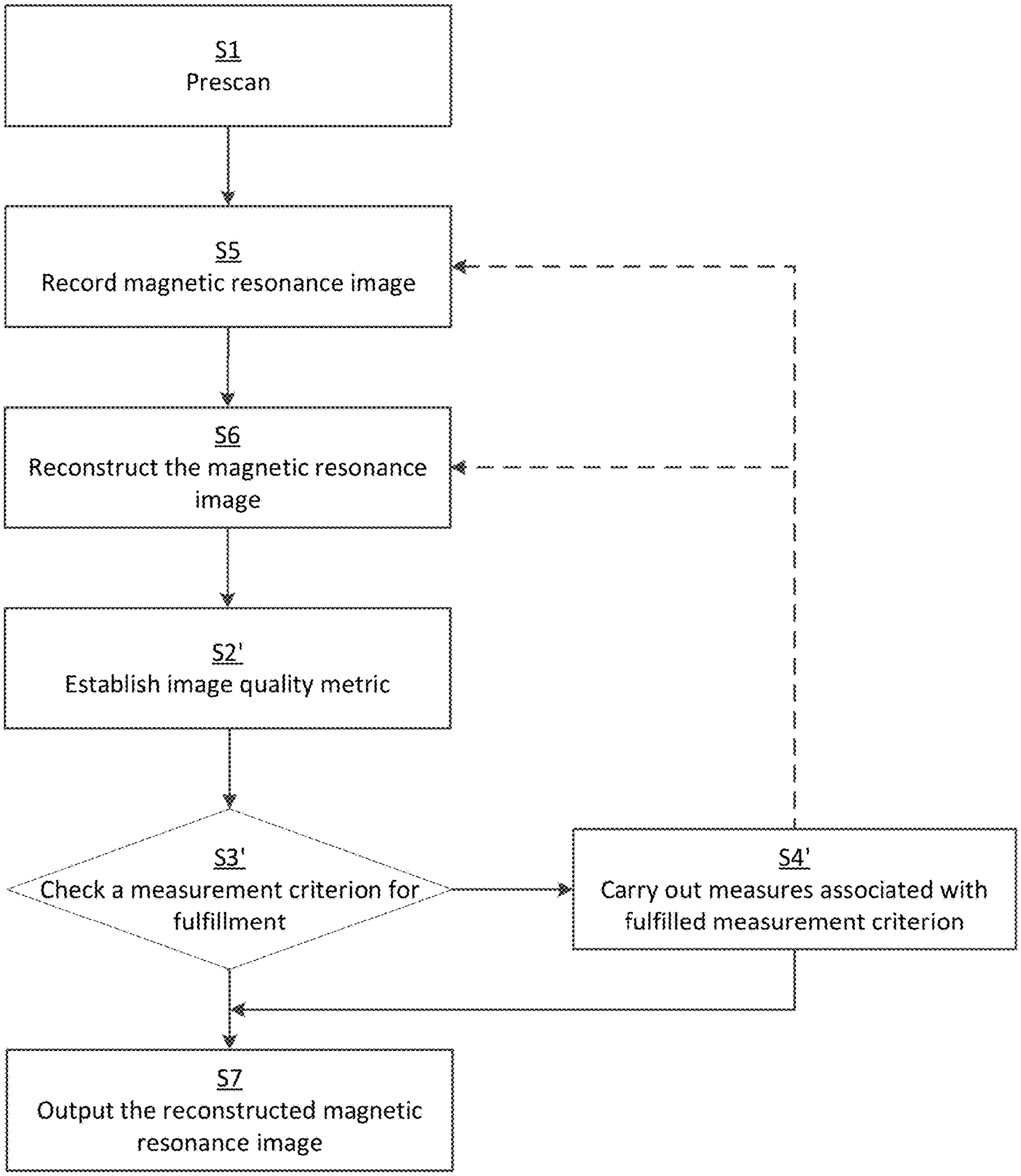
FIG. 2 shows a flow diagram of a second exemplary embodiment of the method according to the disclosure.

FIG. 1 shows a flow diagram of a first exemplary embodiment of the method according to the disclosure. Therein, initially in step S1, as is known with parallel imaging techniques as an accelerating technique but is also utilized with compressed sensing, a prescan takes place. This serves in the present case at least to establish sensitivity information, in particular sensitivity maps, for the receiving coil arrangement used, which comprises a plurality of receiving coils that can be read out individually. The receiving coil arrangement can be, for example, a local coil arrangement in which, when recording a patient, the receiving coils can be positioned as closely as possible to the surface of the patient. The magnetic resonance data recorded in the prescan in step S1 completely samples a lower region of the k-space to be sampled in the image recording procedure, without undersampling, wherein the lower region is typically positioned about the k-space center. From the prescan, regions that are already of interest (ROIs) can also be established despite typically lower spatial resolution. Otherwise, such an ROI established from the magnetic resonance data of a prescan can also restrict the establishment of the image quality metric and/or the use of measure criteria since structural information losses occurring outside the region of interest and/or other image quality losses can be less relevant.

Before the actual raw data is recorded in the image recording procedure, in the present first exemplary embodiment, the magnetic resonance data of the prescan can be evaluated to determine the spatially resolved image quality metric. This takes place in step S2, wherein in the present case by way of example, a spatially resolved geometry factor map is determined as an imaging metric in accordance with the cited article by F. Breuer et al.; alternatively or additionally, a noise map and/or an SNR map, that is a map of the signal-to-noise ratio, can be established.

In step S3, the spatially resolved image quality metric, in this case, the geometry factor map, is then evaluated by way of at least one measure criterion with which a notification and/or adaptation measure is associated, which on its fulfillment is executed in accordance with step S4. In a simple embodiment, it can be provided that in a measure criterion, a simple threshold value check is carried out, which means that it is sufficient for the fulfillment of the measure criterion if a first threshold value is exceeded at least at one image point in the geometry factor map. Preferable thereto and used in the present case, however, are one or both of the following two variants.

Thus in at least one of the at least one measure criterion, it can be provided that it is checked whether at least one second threshold value for at least one specified proportion of the image points of the geometry factor map (or another map) is exceeded or (in the case of a suitable other map, for example, an SNR map) undershot. For this purpose, a histogram of the image quality values of the map, in this case, the geometry factors of the geometry factor map, can be drawn up to be able to judge by simple means what percentage of the geometry factors exceeds the second threshold value.

Particularly advantageous, however, is a variant in which at least one of the at least one measure criterion checks whether the size of at least one cluster of image points in which the image quality values, in this case, geometry factors, exceed a third threshold value exceeds a fourth threshold value. In clusters of this type in the image space, smoothing can occur in the affected image region, and/or other undesirable effects can occur through the noise-reducing effect. It is therefore suitable to detect and localize this in at least one of the at least one measure criterion. For example, clusters of at least 20 image points can be found where the geometry factor exceeds a third threshold value, for example, between two and four. Herein also, an undershoot would naturally be observed in the SNR.

The threshold values in the variants described here of threshold value comparisons in measure criteria can be derived from experiential values and therefore empirically, wherein for example scan results and/or simulations can be evaluated, in particular statistically. In some cases, analytical observations may also be possible.

If none of the measure criteria is fulfilled, the risk of failure to achieve the imaging goal with regard to the noise-reducing effect is very small or non-existent, so then it is possible to proceed directly with the image recording procedure in step S5 and the reconstruction procedure in step S6 without measures being required. If, however, a measure criterion has been fulfilled in step S3, in step S4 the corresponding measures are carried out. In a simple embodiment of this first exemplary embodiment, it is conceivable to use only one notification measure which outputs a notification and/or a warning to a user that with the current settings, the risk exists of a failure to achieve the imaging goal, in particular the loss of relevant structural information. It is extremely advantageous that even before starting the (then possibly not useful) actual image-generating procedure, the information relating to a danger of the failure to achieve the imaging goal is available. The user can then possibly undertake adaptations manually which can then be assessed anew in steps S2 and S3.

In a preferred embodiment, at least one adaptation measure is provided. As an adaptation measure, it can be provided in step S4 to acquire proposals that lead to an improvement in the situation, which can then be adopted completely automatically or after confirmation/selection by the user in order indeed to be able to proceed directly with step S5. For example, an embodiment is conceivable in which, in the manner of an optimization method image-generating parameters, in the present case in particular recording parameters but possibly also reconstruction parameters, are established such that the previously fulfilled measure criterion is no longer fulfilled, wherein it is suitable given a plurality of measure criteria to undertake the establishment of the proposal such that no further measure criterion is fulfilled. For example, the undersampling can be reduced, and/or the phase oversampling can be increased. If relevant, an adaptation of reconstruction parameters can also have the result that relevant restrictions by way of noise-reducing reconstruction techniques are no longer to be expected. Herein, a proposal image quality metric can be established for each potential proposal to determine whether measure criteria are still fulfilled. If there is a plurality of proposals from which the user is to select one, in a combined notification and adaptation measure, a visualization of the effect of the proposals can take place by way of the output of the image quality metric, in this case, the geometry factor map and/or a value derived therefrom, for example, a mean value, which offers the user an improved decision-making basis with regard to the different proposals. For example, a color-coded representation of the geometry factor maps is possible.

In each case, as soon as sufficient adaptations have been made (or the user has decided to accept the risk), the image-generating procedure according to steps S5 (image recording procedure) and S6 (reconstruction procedure) is carried out. In step S7, for example, an output of the reconstructed magnetic resonance image can then take place, whether storage in an internal or external storage means and/or output to a display apparatus and/or an output to further evaluate algorithms.

It should be noted at this point that the method in the first exemplary embodiment and also in the second exemplary embodiment to be described now is carried out by way of the control apparatus of the magnetic resonance apparatus being used.

In the second exemplary embodiment which will now be described, information from the reconstruction procedure can also be incorporated into the establishment of the image quality metric (and/or at least one part of the image quality metric), which means that for establishing the image quality metric, the magnetic resonance image generated by way of the image-generating procedure (steps S5 and S6) should also be included. As distinct from the first exemplary embodiment, therefore, immediately following the prescan in step S1, the image recording procedure for recording the raw data (step S5) takes place, and thereafter the reconstruction procedure (step S6) uses the trained reconstruction function. Only thereafter is the image quality metric established in step S2'. This can naturally also contain one of the maps (geometry factor map, noise map, and/or SNR map) mentioned with the first exemplary embodiment, which can also be evaluated by way of corresponding measure criteria. Particularly advantageously, however, at least one image quality metric is determined, which also or alone evaluates the magnetic resonance image. In this regard, some specific possibilities exist for further maps offering spatial resolution, particularly a confidence map and/or at least one similarity map.

A further neural network has been trained in advance of this second exemplary embodiment to establish a confidence map, which is associated with the trained reconstruction function, specifically a confidence establishment function. The trained confidence establishment function uses the magnetic resonance image as input data and supplies a confidence map aligned to the issue of a possible failure to achieve the imaging goal as output data.

Furthermore, it is also possible to fit the magnetic resonance image in the k-space (possibly after an inverse transform thereinto) to the lower region sampled in the prescan of step S1. Expressed differently, a fitting of the reconstructed k-space to the size of the k-space of the prescan takes place. This enables the image spaces of the magnetic resonance data cut to size in this manner and the magnetic resonance data of the prescan to be subsequently compared for deviations, for example, using structural similarity as a similarity measure. In this way, a first similarity map comes into existence. Once the lower region of the k-space has indeed been completely sampled in the prescan, the similarity map shows any existing information loss.

However, in addition to the reconstruction procedure of step S6, it is additionally or alternatively possible in step S2' to undertake a "conventional" reconstruction of a comparison image, wherein the noise-reducing reconstruction technique, in this case, the trained reconstruction function, is not used. Known reconstruction techniques of parallel imaging, for example, GRAPPA, can be used herein. At least one second similarity map can then be established by establishing a similarity map of this comparison image with the magnetic resonance data of the prescan (again suitably after corresponding fitting to size) and/or with the magnetic resonance image. The underlying idea here is that in regions in which in particular there is a threat of the loss of structural information, such huge differences already occur, for example, by way of severe noise interference based on the undersampling in the accelerating technique, that such "problem zones" can be directly recognized.

In step S3', similarly to step S3, at least one measure criterion is again checked for fulfillment, wherein threshold-based embodiments, as already described in relation to step S3, can also be used for the confidence map and/or the at least one similarity map, wherein confidence threshold values and/or similarity threshold values are then used accordingly.

In step S4', measures associated with fulfilled measure criteria are again carried out. Apart from the notification and/or information measures described in relation to step S4 for the information of a user, the output and/or use of a proposal for adapting image-generating parameters and/or an automatic adaptation of image-generating parameters, other measures, in particular other adaptation measures, are also conceivable in this second exemplary embodiment.

Thus, for example, it can be checked as an adaptation measure whether reconstruction parameters for the reconstruction procedure (step S6) can be adapted such that on a renewed reconstruction of an improved image with these adapted reconstruction parameters, an improved image quality metric also results, in which case the previous magnetic resonance image is then discarded and can be replaced with the improvement image. This procedure can also take place iteratively until no further measure criteria are fulfilled. Herein also, if useful, a confirmation by the user can naturally be repeated; in any case, it is suitable to output notifications to him for information. In this way, it is possible to work with the raw data already recorded without having to initiate a complete or partial re-recording.

In particular, in cases in which such an adaptation of reconstruction parameters is insufficient, adaptation measures are also conceivable in which the raw database is adapted by supplementation. This means that, following the reconstruction procedure in step S6, by way of a corresponding adaptation measure, k-space data still to be supplemented can be recorded as raw data, for example, to reduce the effective undersampling, whereupon with this additional raw data, a renewed reconstruction is then carried out in the reconstruction procedure and the assessment can be repeated in steps S2' and S3'. Thus at least the quantity of further raw data required can be reduced.

If no further measure criteria are fulfilled and/or if no adaptation takes place by way of the measures, finally in step S7, an output of the magnetic resonance image can take place as described in the first exemplary embodiment.

Figure 3:
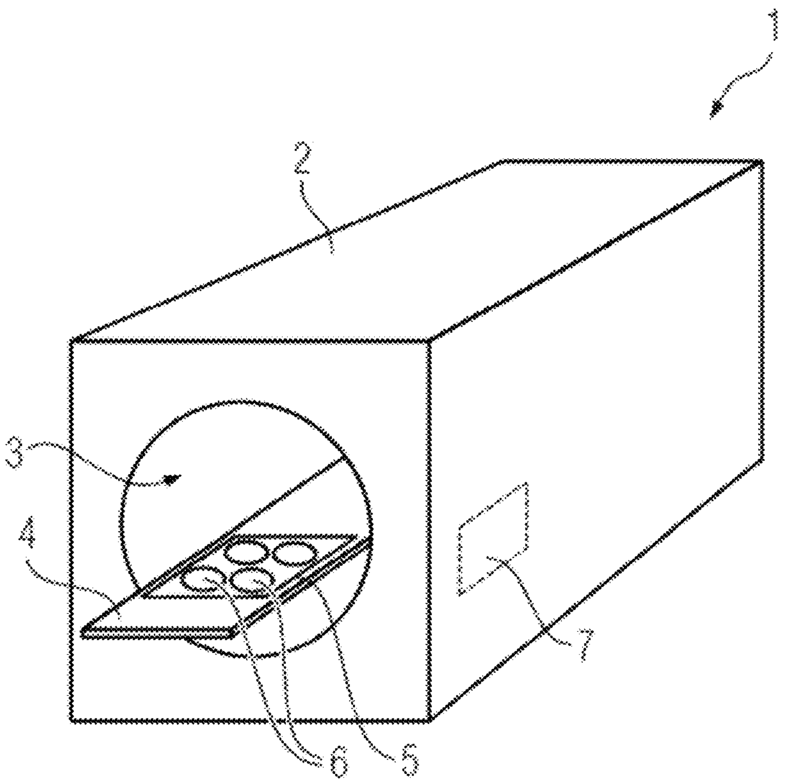
FIG. 3 shows a magnetic resonance apparatus according to the disclosure.

FIG. 3 shows a sketch of the principle of a magnetic resonance apparatus 1 according to the disclosure. This has, as known in principle, a main magnet unit 2 which comprises the main magnet generating the main magnetic field, and a cylindrical patient receiving region 3 into which a patient to be examined can be moved using a patient support 4. A high-frequency coil arrangement and a gradient coil arrangement can also be provided surrounding the patient receiving space 3, although, for the sake of simplicity, these are not shown in detail here. What is shown here, however, is a receiving coil arrangement 5 designed as a local coil which has a plurality of individual receiving coils 6 which can be placed close to the surface of the patient in the receiving region and the sensitivity information of which can be determined in the prescan of step S1.

Figure 4:
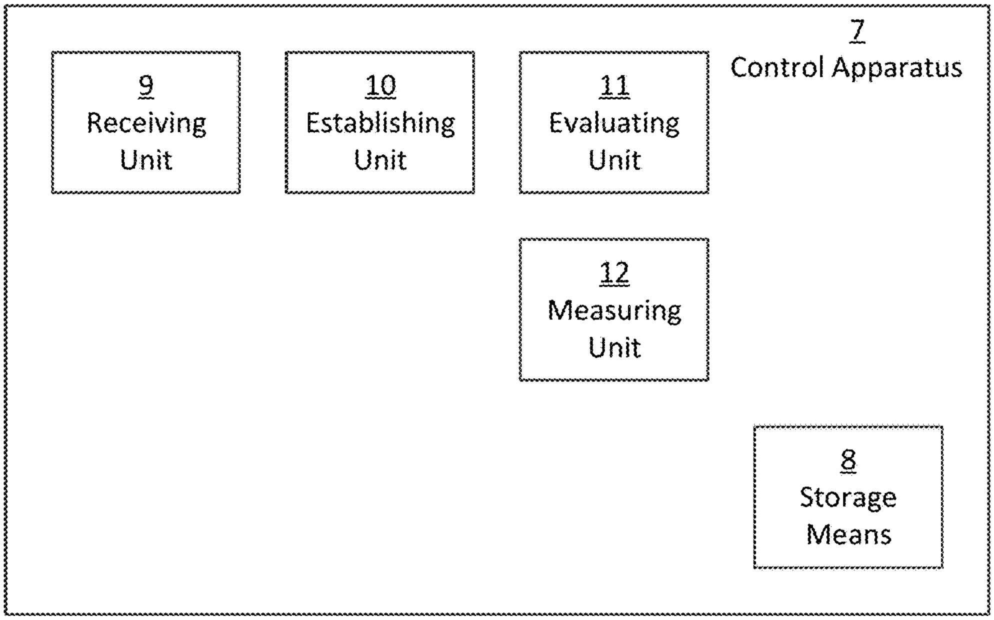
FIG. 4 shows the functional structure of a control apparatus of the magnetic resonance apparatus.

The operation of the magnetic resonance apparatus 1 is controlled by way of a control apparatus 7 which is designed for carrying out the method according to the disclosure and the corresponding functional structure of which is shown in more detail in FIG. 4. Apart from a processor, by way of which corresponding functional units which will be described below can be realized, the control apparatus 7 also comprises a storage means 8 in which intermediate results such as the image quality metric can be stored.

As functional units, the control apparatus 7 first has a receiving unit 9, which controls the receiving operation of the magnetic resonance apparatus 1, particularly in steps S1 and S5. Since such a receiving unit 9 implements magnetic resonance sequences in the context of a scan protocol, it can also be designated a sequence unit.

In an establishing unit 10, the image quality metric can be established in accordance with steps S2, S2'. Accordingly, an evaluating unit 11 can also be provided in which the at least one measure criterion is evaluated, cf. steps S3, S3'. In a measuring unit 12, when a measure criterion is fulfilled, the notification and/or adaptation measures associated therewith are carried out, cf. steps S4, S4'.

Although the disclosed aspects have been illustrated and described in detail using the preferred exemplary embodiment, the disclosure is not restricted by the examples disclosed. Other variations can be derived herefrom by a person skilled in the art without departing from the protective scope of the disclosure.

The invention claimed is:

1. A computer-implemented method for assessing an image-generating procedure of magnetic resonance imaging, wherein in the image-generating procedure, an image recording procedure using at least one accelerating technique is combined with a reconstruction procedure including a reconstruction function trained using machine learning, comprising:
  - establishing a spatially resolved image quality metric for a magnetic resonance image generated with the image-generating procedure;
  - evaluating the image quality metric using at least one measure criterion with which at least one notification and/or adaptation measure is associated; and
  - carrying out the at least one notification and/or adaptation measure for each fulfilled measure criterion,
  - wherein at least one of the at least one measure criterion is checked for a presence of an excessively high risk of at least partial loss of structural information that is to be imaged in a recording region using an accelerating technique and/or noise reduction and/or in that establishment and evaluation of the quality metric and, if at least one measure criterion is fulfilled, execution of an associated notification and/or adaptation measure takes place before the execution of the recording procedure, immediately following a prescan.

2. The method as claimed in claim 1, wherein the image quality metric is established from magnetic resonance data of a prescan, comprising a complete sampling of a lower region of k-space to be sampled and/or for establishing reconstruction parameters to be used in the reconstruction procedure and/or from the magnetic resonance image.

3. The method as claimed in claim 2, wherein as the image quality metric, a geometry factor map and/or a noise map, and/or an SNR map of a signal-to-noise ratio is established only from the magnetic resonance data of the prescan.

4. The method as claimed in claim 3, wherein at least one of the at least one measure criterion checks for at least one of at least one map of the image quality metric whether:
  - at least one first threshold value is exceeded or undershot for at least one image point of the map; and/or
  - at least one second threshold value is exceeded or undershot for at least one specified proportion of the image points; and/or
  - whether a size of at least one cluster of image points in which a third threshold value is exceeded or undershot exceeds a fourth threshold value.

5. The method as claimed in claim 2, wherein a confidence map of the magnetic resonance image is established as the image quality metric, using a trained confidence establishment function.

6. The method as claimed in claim 2, wherein the magnetic resonance image is cut to size to the lower region and using a comparison with the magnetic resonance data of the prescan, a first similarity map is established as the image quality metric and/or in that in addition to the establishment of the magnetic resonance image, an establishment of a comparison image takes place in a reconstruction procedure without using the reconstruction function trained using machine learning and using a comparison of the comparison image with the magnetic resonance data of the prescan and/or with the magnetic resonance image, at least one second similarity map is established.

7. The method as claimed in claim 1, wherein the at least one notification measure comprises an output of a warning and/or a notification to a user.

8. The method as claimed in claim 1, wherein at least one notification and/or adaptation measure comprises establishment of at least one proposal for at least one recording parameter of a recording procedure and/or at least one reconstruction parameter of the reconstruction procedure, wherein the at least one proposal is used automatically and/or after confirmation by a user after an output to the user for adapting image-generating parameters and an image generation takes place.

9. The method as claimed in claim 8, wherein the establishment of the proposal takes place such that at least a previously fulfilled measure criterion is no longer fulfilled when using the proposal, and no further measure criterion is fulfilled.

10. The method as claimed in claim 8, wherein for a plurality of proposals using magnetic resonance data of a prescan, proposal image quality metrics are established and are visualized to a user for selection of at least one of the at least one proposal regarding recording parameters.

11. The method as claimed in claim 8, wherein for exclusively at least one proposal regarding at least one reconstruction parameter, for this an improvement image is generated in a renewed reconstruction procedure and an improvement image quality metric is established, wherein for an improvement image quality metric indicating an improvement relative to the original image quality metric of the magnetic resonance image, the original magnetic resonance image is discarded, and the improvement image is used as the magnetic resonance image.

12. The method as claimed in claim 1, wherein at least one adaptation measure relates to recording of additional raw data, reducing undersampling in an additional recording procedure.

13. A magnetic resonance apparatus, comprising a controller configured to carry out a method as claimed in claim 1.

14. A non-transitory electronically readable data carrier on which a computer program is stored, wherein the computer program carries out steps of the method as claimed in claim 1 when the program is executed on a controller of a magnetic resonance apparatus.

* * * * *